United States Patent
Park

(10) Patent No.: US 11,410,018 B2
(45) Date of Patent: Aug. 9, 2022

(54) METHOD, APPARATUS, AND SYSTEM FOR INFERRING CONTAMINATED AIR EXPOSURE LEVEL BASED ON OPERATION INFORMATION OF WEARABLE DEVICE OR PORTABLE AIR PURIFIER

(71) Applicant: LG Electronics Inc., Seoul (KR)

(72) Inventor: Yun Sik Park, Seoul (KR)

(73) Assignee: LG Electronics Inc., Seoul (KR)

( * ) Notice: Subject to any disclaimer, the term of this patent is extended or adjusted under 35 U.S.C. 154(b) by 209 days.

(21) Appl. No.: 16/600,001

(22) Filed: Oct. 11, 2019

(65) Prior Publication Data
US 2020/0042861 A1 Feb. 6, 2020

(30) Foreign Application Priority Data
Aug. 26, 2019 (KR) .................. 10-2019-0104525

(51) Int. Cl.
*G01N 33/00* (2006.01)
*G06N 3/04* (2006.01)
*G06N 3/08* (2006.01)

(52) U.S. Cl.
CPC ........... *G06N 3/04* (2013.01); *G01N 33/0062* (2013.01); *G06N 3/08* (2013.01)

(58) Field of Classification Search
CPC .......... G06N 3/04; G06N 3/0454; G06N 3/08; G06N 3/088; G06N 7/005; G01N 33/0062; G01N 15/02; G01N 15/06; G01N 1/26; G01N 2015/1486
USPC ...... 73/31.01; 340/586; 702/1–2, 23–24, 26, 702/29, 127, 150, 189
See application file for complete search history.

(56) References Cited

U.S. PATENT DOCUMENTS

| | | | | |
|---|---|---|---|---|
| 2002/0144537 A1* | 10/2002 | Sharp | .................. | G01N 33/0034 73/31.01 |
| 2006/0137521 A1* | 6/2006 | Sung | .................. | B01D 46/0038 95/1 |
| 2013/0174646 A1* | 7/2013 | Martin | .................... | G01N 33/00 73/31.02 |
| 2017/0372216 A1* | 12/2017 | Awiszus | .................. | A62B 27/00 |
| 2018/0001049 A1* | 1/2018 | Schuller | .................. | A62B 9/006 |
| 2018/0217617 A1* | 8/2018 | Blackley | ............. | B01F 3/04007 |

(Continued)

FOREIGN PATENT DOCUMENTS

KR 1020170077691 7/2017

*Primary Examiner* — Jeffrey P Aiello
(74) *Attorney, Agent, or Firm* — Fish & Richardson P.C.

(57) ABSTRACT

A contaminated air exposure level inferring apparatus may include a receiver for receiving a fine dust concentration measured from a fine dust sensor of the wearable device or the portable air purifier, an exposure level classifier for inferring a contaminated air exposure level of a user holding the wearable device or the portable air purifier based on the measured fine dust concentration, and a communicator for communicating with a server. The server may include an artificial intelligence model learner for generating an artificial intelligence model that has learned data on the measured fine dust concentration through a deep neural network. According to the present disclosure, it is possible to infer the contaminated air exposure level of the user of the wearable device or the portable air purifier by using artificial intelligence (AI), a contaminated air exposure level inferring technology based on the artificial intelligence, and a 5G network.

12 Claims, 7 Drawing Sheets

(56) References Cited

U.S. PATENT DOCUMENTS

| | | | | |
|---|---|---|---|---|
| 2019/0117815 A1* | 4/2019 | Wei | ............................ | F24F 11/00 |
| 2019/0156600 A1* | 5/2019 | Potyrailo | ................. | B61C 17/08 |
| 2019/0301761 A1* | 10/2019 | Scheja | ....................... | F24F 8/10 |
| 2019/0381443 A1* | 12/2019 | Kim | ...................... | B01D 46/429 |
| 2020/0323701 A1* | 10/2020 | Jastrzebski | .............. | A61F 13/42 |

* cited by examiner

METHOD, APPARATUS, AND SYSTEM FOR INFERRING CONTAMINATED AIR EXPOSURE LEVEL BASED ON OPERATION INFORMATION OF WEARABLE DEVICE OR PORTABLE AIR PURIFIER

CROSS-REFERENCE TO RELATED APPLICATION

This application claims benefit of priority to Korean Patent Application No. 10-2019-0104525, filed on Aug. 26, 2019, the entire disclosure of which is incorporated herein by reference.

BACKGROUND

1. Technical Field

The present disclosure relates to a method, an apparatus and a system for inferring a contaminated air exposure level, and more particularly, to a method, an apparatus, and a system for inferring a contaminated air exposure level of a person holding a wearable device or a portable air purifier (hereinafter, referred to as 'user') based on the operation information of a wearable device or a portable air purifier.

2. Description of-related Art

As the industry develops, air contamination is getting serious. There are many types of air pollutants that float in the air, but scientists are largely classified into gaseous substances such as sulfur dioxide, carbon monoxide, or ozone, and particulate substances such as fine dust or ultra-fine dust. Most gaseous substances come from human daily life and industrial activities, while particulate substances are very complex in origin. Much of the particulate substances come from human activity in industrial parks and metropolitan cities, but may be created from natural phenomena such as yellow dust or volcanic activity, or dust from the surface may be swept into the air by the wind.

As the air contamination due to dust is getting serious, the government has actually started to measure dust among air pollutants, and provides information on yellow dust, fine dust (PM10 or less), and ultra-fine dust (PM2.5 or less).

Conventionally, home appliances have been linked with reference to utilization of weather information on the air contamination level or the result of a portable dust sensor.

There is disclosed in the-related art that a conventional air purifier receives air contamination level information from the outside, accurately measures the substances contained in contaminated air by using fine dust information and air contamination level information, and efficiently purifies the air. However, since the actual user may not determine that stayed in the area how severe the air contamination level was, the air purifier of the-related art 1 merely provided a control method for purifying the air depending on the weather information groovily.

As described above, since fine dust information and air contamination information were used in the-related art, there was drawback that it was difficult for an actual user to confirm the level of exposure to air contaminated by outdoor activities.

SUMMARY OF THE DISCLOSURE

An object of an embodiment of the present disclosure is to recognize the effect on dust sensor information and an air purifier function of a wearable device or a portable air purifier to confirm the level to which the user holding the portable air purifier has been exposed to contaminated air.

Another object of an embodiment of the present disclosure is to share the corresponding information with various clothing-related home appliances and air purification-related home appliances to automatically execute a fine dust course of a clothing manager/a washing machine/an air purifier when interlocked.

Still another object of an embodiment of the present disclosure is to predict the contaminated air exposure level in advance by using the dust sensor information of the wearable device or the portable air purifier, usage amount of a filter of the portable air purifier of the portable air purifier, etc.

Yet another object of an embodiment of the present disclosure is to maintain the user's health and to more conveniently use clothing and air purification-related home appliances by using an artificial intelligence technology.

The present disclosure is not limited to what has been described above, and other aspects and advantages of the present disclosure will be understood by the following description and become apparent from the embodiments of the present disclosure. Furthermore, it will be understood that aspects and advantages of the present disclosure may be achieved by the means set forth in claims and combinations thereof.

A contaminated air exposure level inferring method, apparatus, and system according to an embodiment of the present disclosure for achieving the objects disclose a method for inferring a contaminated air exposure level and a contaminated air exposure level inferring apparatus based on operation information of a wearable device or a portable air purifier for inferring the contaminated air exposure level based on an AI technology.

Specifically, a method for inferring a contaminated air exposure level based on operation information of a wearable device or a portable air purifier may include receiving a fine dust concentration measured from a fine dust sensor of a wearable device or a portable air purifier, inferring a contaminated air exposure level of a user based on the fine dust concentration, and notifying the user of information on the inferred contaminated air exposure level or transferring information on the inferred contaminated air exposure level to a clothing-related device or an air purification-related device when the inferred contaminated air exposure level of the user exceeds a predetermined threshold.

A contaminated air exposure level inferring apparatus according to another embodiment of the present disclosure may include a receiver for receiving a fine dust concentration measured from a fine dust sensor of a wearable device or a portable air purifier, an exposure level classifier for inferring a contaminated air exposure level of a user holding the wearable device or the portable air purifier based on the fine dust concentration, and a communicator for transferring information on the inferred contaminated air exposure level to a clothing-related device or an air purification-related device when the inferred contaminated air exposure level of the user exceeds a predetermined threshold.

A contaminated air exposure level inferring system according to still another embodiment of the present disclosure may include a contaminated air exposure level inferring apparatus based on operation information of a wearable device or a portable air purifier, and a server for collecting the operation information of the wearable device or the portable air purifier and learning an artificial intelligence model for inferring the contaminated air exposure level, the contaminated air exposure level inferring apparatus may include a receiver for receiving a fine dust concentration measured from a fine dust sensor of the wearable device or the portable air purifier, an exposure level classifier for inferring a contaminated air exposure level of a user holding the wearable device or the portable air purifier based on the measured fine dust concentration, and a communicator for communicating with the server, the communicator transmitting the fine dust concentration to the server, and the server may include an artificial intelligence model learner for generating an artificial intelligence model that has learned data on the measured fine dust concentration through an artificial intelligence algorithm in order to infer the contaminated air exposure level of the user, the server may be configured to transmit the learned artificial intelligence model that has learned through the artificial intelligence model learner to the contaminated air exposure level inferring apparatus, and the exposure level classifier of the contaminated air exposure level inferring apparatus may be configured to infer the contaminated air exposure level through the learned artificial intelligence model received from the server.

In addition, other methods and systems for implementing the present disclosure, and a computer program for executing such methods, may be provided.

Other aspects, features, and advantages other than those described above will become apparent from the following drawings, claims, and detailed description of the present disclosure.

According to an embodiment of the present disclosure, it is possible to infer the contaminated air exposure level of the user by using the artificial intelligence (AI), the AI based contaminated air exposure level inferring technology, and the 5G network.

According to an embodiment of the present disclosure, it is possible to recognize the exposure level to the actual contaminated air of the user to automatically execute the optimal course at the time of interlocking with various clothing-related home appliances and air purification-related home appliances.

According to an embodiment of the present disclosure, it is possible to collect the dust sensing information and the air purifier operation information of the portable air purifiers within a certain area through a data storage device such as a cloud server to forecast an air contamination level to user.

The effects of the present disclosure are not limited to the effects mentioned above, and other effects not mentioned may be clearly understood by those skilled in the art from the following description.

DETAILED DESCRIPTION

Figure 1:
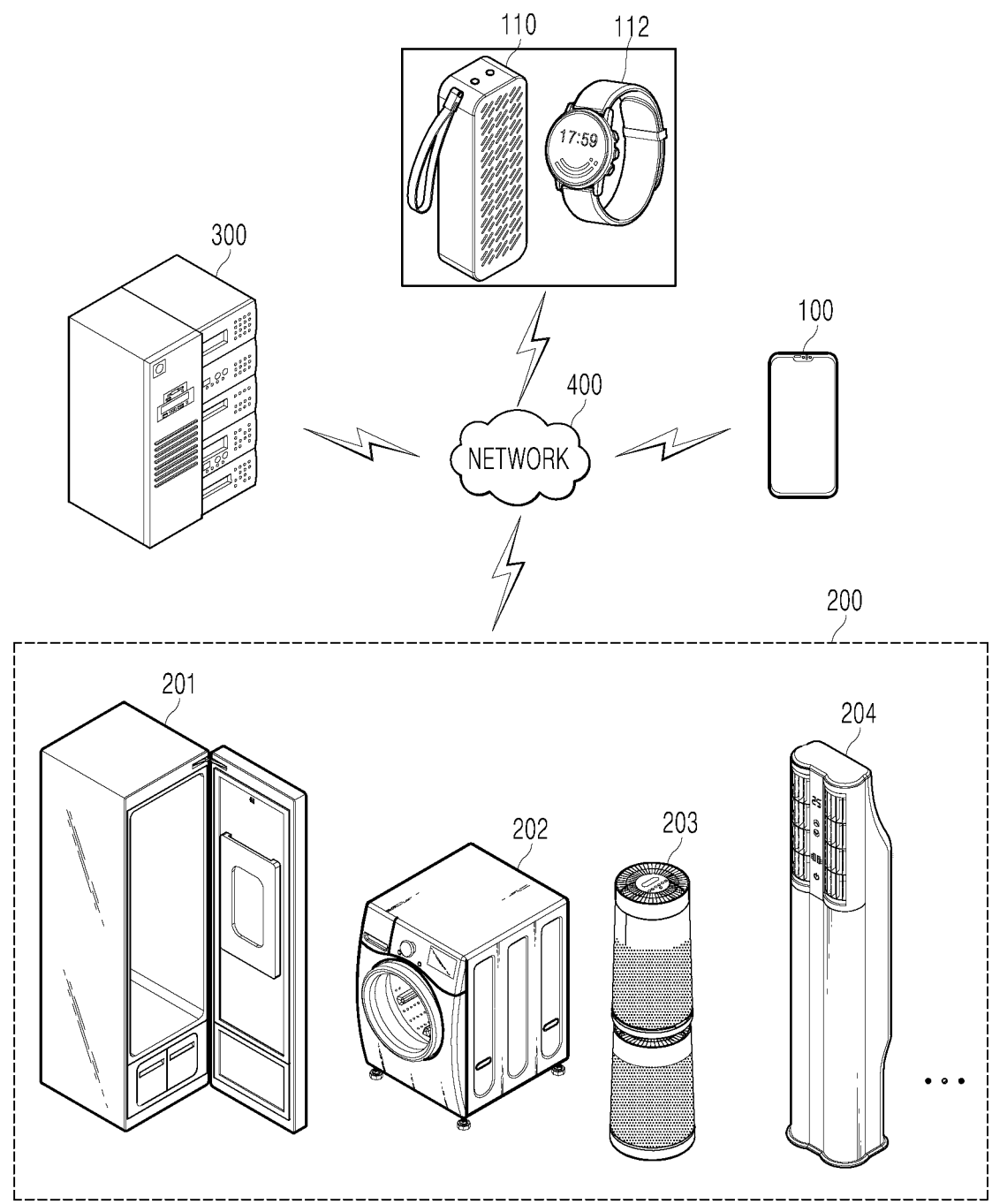
FIG. 1 is an exemplary diagram of a system environment including a contaminated air exposure level inferring apparatus, a portable air purifier or a wearable device, a clothing-related home appliance, an air purification-related home appliance, a server, and a network for communicatively connecting them according to an embodiment of the present disclosure.

Advantages and features of the present disclosure and methods for achieving them will become apparent from the descriptions of aspects hereinbelow with reference to the accompanying drawings. However, the description of particular example embodiments is not intended to limit the present disclosure to the particular example embodiments disclosed herein, but on the contrary, it should be understood that the present disclosure is to cover all modifications, equivalents and alternatives falling within the spirit and scope of the present disclosure. The example embodiments disclosed below are provided so that the present disclosure will be thorough and complete, and also to provide a more complete understanding of the scope of the present disclosure to those of ordinary skill in the art. In the interest of clarity, not all details of the relevant art are described in detail in the present specification in so much as such details are not necessary to obtain a complete understanding of the present disclosure.

The terminology used herein is used for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "includes," "including," "containing," "has," "having" or other variations thereof are inclusive and Accordingly specify the presence of conditioned features, integers, steps, operations, elements, and/or components, but do not preclude the presence or addition of one or more other features, integers, steps, operations, elements, components, and/or groups thereof. Furthermore, these terms such as "first," "second," and other numerical terms, are used only to distinguish one element from another element. These terms are generally only used to distinguish one element from another.

Hereinafter, embodiments of the present disclosure will be described in detail with reference to the accompanying drawings. Like reference numerals designate like elements throughout the specification, and overlapping descriptions of the elements will not be provided.

FIG. 1 is an exemplary diagram of a system environment including a contaminated air exposure level inferring apparatus, a portable air purifier or a wearable device, a clothing-related home appliance, an air purification-related home appliance, a server, and a network for communicatively connecting them according to an embodiment of the present disclosure.

A contaminated air exposure level inferring apparatus 100 or a contaminated air exposure level inferring system may determine whether it is a precise dynamic horizontal failure by using big data, an artificial intelligence (AI) algorithm and/or a machine learning algorithm in a 5G environment connected for the Internet of Things. The contaminated air exposure level inferring apparatus 100 may be installed in an application app form in a user terminal, and embedded in a portable air purifier 110 or a wearable device 112.

Referring to FIG. 1, a driving environment 1 of a contaminated air exposure level inferring system may include the contaminated air exposure level inferring apparatus 100, clothing and air purification-related home appliances 200, a server 300, and a network 400. A clothing-related home appliance of the clothing and air purification-related home appliances 200 may include a clothing manager 201 and a washing machine 202, and the air purification-related home appliance may include an air purifier 203 and an air conditioner 204, etc. The contaminated air exposure level inferring apparatus 100 may include a communicator 125, and transmit sensor data of the contaminated air exposure level inferring apparatus 100 to the server 300 through the wired or wireless network 400, and the server 300 may transmit various air contamination-related information and a learned artificial intelligence model to the clothing and air purification-related home appliance 200 such as the contaminated air exposure level inferring apparatus 100 or the washing machine.

In an embodiment of the present disclosure, the contaminated air exposure level inferring apparatus 100 may receive information on an air contamination level from the portable air purifier 110 and the wearable device 112 to communicate with the clothing and air purification-related home appliance 200 and the server 300 through the network 400, and may perform machine learning such as Deep Learning, and the memory 121 may store data used for machine learning, result data, etc.

The server 300 may be a database server for providing big data necessary for applying various artificial intelligence algorithms and data for operating the contaminated air exposure level inferring apparatus 100. In addition, the server 300 may include a web server or an application server so as to remotely control the operation of the contaminated air exposure level inferring apparatus 100 by using a contaminated air exposure level inferring application or a contaminated air exposure level inferring web browser installed in the user terminal.

Artificial intelligence (AI) is an area of computer engineering science and information technology that studies methods to make computers mimic intelligent human behaviors such as reasoning, learning, self-improving, and the like.

In addition, artificial intelligence does not exist on its own, but is rather directly or indirectly-related to a number of other fields in computer science. In recent years, there have been numerous attempts to introduce an element of AI into various fields of information technology to solve problems in the respective fields.

Machine learning is an area of artificial intelligence that includes the field of study that gives computers the capability to learn without being explicitly programmed. More specifically, machine learning is a technology that investigates and builds systems, and algorithms for such systems, which are capable of learning, making predictions, and enhancing their own performance on the basis of experiential data. Machine learning algorithms, rather than executing rigidly-set static program commands, may take an approach that builds a specific model based on input data for deriving a prediction or decision.

The network 400 may serve to connect the portable air purifier 110, the wearable device 112, the contaminated air exposure level inferring apparatus 100, the clothing and air purification-related home appliance 200, and the server 300. The network 400 may include, for example, wired networks such as local area networks (LANs), wide area networks (WANs), metropolitan area networks (MANs), and integrated service digital networks (ISDNs), or wireless networks such as wireless LANs, CDMA, Bluetooth, and satellite communication, but the scope of the present disclosure is not limited thereto. Furthermore, the network 400 may transmit and receive information using short-range communications or long-distance communications. Here, the short-range communications may include Bluetooth, radio frequency identification (RFID), infrared data association (IrDA), ultra-wideband (UWB), ZigBee, and wireless fidelity (Wi-Fi) technology. The long-distance communications may include code division multiple access (CDMA), frequency division multiple access (FDMA), time division multiple access (TDMA), orthogonal frequency division multiple access (OFDMA), and single carrier frequency division multiple access (operation SC-FDMA) technology.

The network 400 may include a connection of network elements such as a hub, a bridge, a router, a switch, and a gateway. The network 400 may include one or more connected networks, for example, a multi-network environment, including a public network such as an internet and a private network such as a safe corporate private network. The access to the network 400 may be provided via one or more wired or wireless access networks. Furthermore, the network 400 may support the Internet of things (IoT) for 5G communication or exchanging and processing information between distributed elements such as objects.

Figure 2:
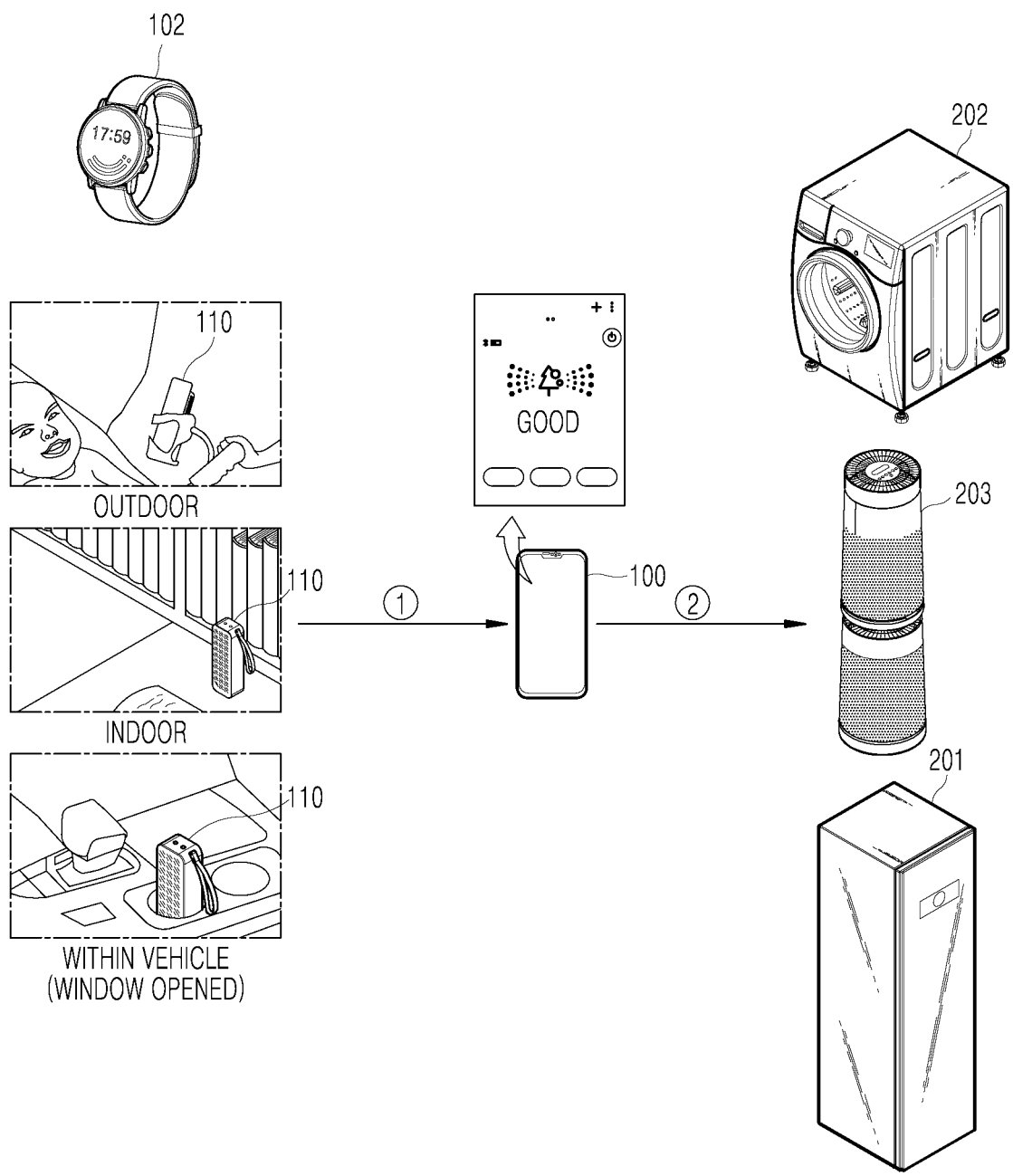
FIG. 2 is an exemplary diagram showing an interlocking process from the contaminated air exposure level inferring apparatus to the clothing and air purification-related home appliances with information of an air contamination level sensing sensor according to an embodiment of the present disclosure.

FIG. 2 is an exemplary diagram showing an interlocking process from the contaminated air exposure level inferring apparatus to the clothing and air purification-related home appliances with information of an air contamination level sensing sensor according to an embodiment of the present disclosure.

In an embodiment of the present disclosure, the fine dust concentration, the intensity of a fan, and usage amount of a filter of the portable air purifier of the portable air purifier 110 used during the outdoor activity of the user may be a reference for inferring the level at which the user has been exposed to the contaminated air.

The contaminated air exposure level inferring apparatus 100 may receive data on the fine dust concentration from a dust sensor mounted on the wearable device 112, such as a smart watch, or a dust sensor mounted on the portable air purifier 110, additionally receive data on the intensity of the fan and the amount of the filter used from the portable air purifier 110 (①), infer the contaminated air exposure level of the user based on at least one among the data on the fine dust concentration, and the data on the intensity of the fan or the amount of the filter used, and transfer information on the contaminated air exposure level to the external home appliances 200 such as the clothing and air purification-related home appliances such as the clothing manager 201, the washing machine 202, the air purifier 203, and the air conditioner 204 through Wi-Fi, Bluetooth, IoT, or 5G communication when the inferred contaminated air exposure level of the user exceeds a predetermined threshold (②).

In an embodiment of the present disclosure, the contaminated air exposure level inferring apparatus 100 and the server 300 may receive data on at least one among the fine dust concentration, the intensity of the fan, or the amount of the filter used of the portable air purifier 110 used during outdoor activities of the user when the user has operated the air purification-related home appliances 203, 204 immediately after the outdoor activity to learn an artificial intelligence model for inferring the contaminated air exposure level of the user.

The external home appliance 200 such as the clothing and air purification-related home appliances receiving information on the contaminated air exposure level may notify the user of at least one among the information of the fine dust sensor, the dust improvement effect by air purification of the portable air purifier, or the contaminated air exposure level per hour. In addition, the external home appliance 200 such as interlocked clothing and air purification-related home appliances may automatically execute a fine dust-related optima course by matching the inferred contaminated air exposure level result to the external home appliance 200 such as the clothing and air purification-related home appliances.

Figure 3A:
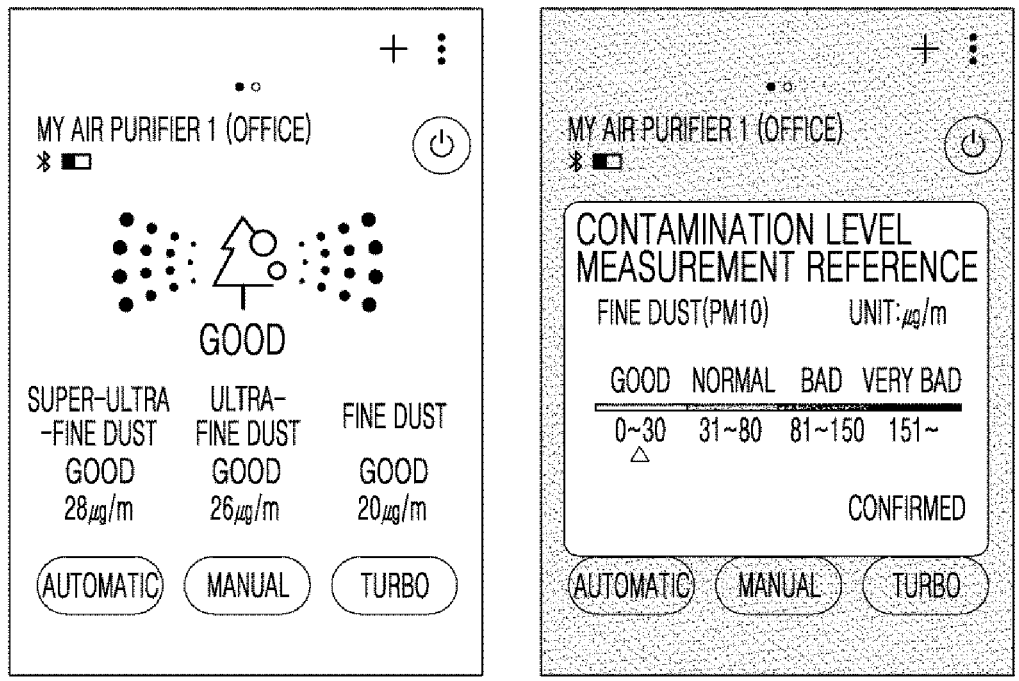
FIG. 3A is an exemplary diagram showing a fine dust concentration of the portable air purifier used in an embodiment of the present disclosure.

FIG. 3A is an exemplary diagram showing a fine dust concentration of the portable air purifier used in an embodiment of the present disclosure.

A fine dust concentration may be expressed as $\mu g/m^3$. The portable air purifier 110 may divide the fine dust (PM10) by a section by concentration to be expressed as 'good (0 to 30 μg)', 'normal (31 to 80 μg)', 'bad (81 to 150 μg)', and 'very bad (151 μg or more). In addition, the portable air purifier 110 may measure super-ultra-fine dust, ultra-fine dust, and fine dust. In addition, the current fine dust purification state may be displayed.

In an embodiment of the present disclosure, the fine dust concentration of the portable air purifier may be measured differently in addition to the concentration. For example, it may be expressed as μm (micrometers). The fine dust may be classified into fine dust (PM10) and ultra-fine dust (PM2.5) according to the size (μm). In addition, the size of the ultra-fine dust may be classified as PM1.0. The size of the fine dust is often expressed by adding a number after Particulate Matter (PM). For example, 'PM10' means fine dust of 10 μm or less and 'PM2.5' means ultra-fine dust of 2.5 μm or less. 'PM2.5 value' refers to 'ultra-fine dust value.' In the present disclosure, the fine dust is defined as including both the fine dust and the ultra-fine dust.

In an embodiment of the present disclosure, the contaminated air exposure level of the user may be inferred based on a plurality of fine dust concentrations according to the size of the fine dust. For example, the contaminated air exposure level may be inferred by monitoring a fine dust concentration per a specific hour. For example, in the contaminated air exposure level classification, the level of the ultra-fine dust (PM2.5) per 1 hour may be classified into level 1: good (0 to 15 $\mu g/m^3$), level 2: normal (16 to 35 $\mu g/m^3$), level 3: high (36 to 75 $\mu g/m^3$), and level 4: very high (76 $\mu g/m^3$ or more).

When the inferred contaminated air exposure level of the user exceeds a predetermined threshold, the user may be notified of the information on the inferred contaminated air exposure level. In addition, the range of the contaminated air exposure level may be used as a predetermined threshold to be transferred to the external home appliance 200 such as clothing and air purification-related home appliances. The determination of whether to exceed the predetermined threshold may determine whether the fine dust concentration exceeds a specific value for a specific time. For example, when the ultra-fine dust value is equal to or larger than the range of the bad per 1 hour (36 $\mu g/m^3$), it may instruct the external home appliance 200 such as clothing and air purification-related home appliances to automatically execute an air contamination-related course.

Figure 3B:
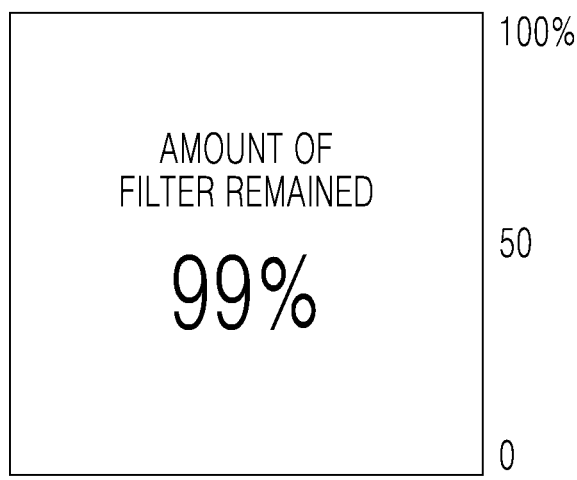
FIG. 3B is an exemplary diagram showing usage amount of a filter of the portable air purifier of the portable air purifier used in an embodiment of the present disclosure.

FIG. 3B is an exemplary diagram showing usage amount of a filter of the portable air purifier of the portable air purifier used in an embodiment of the present disclosure.

The portable air purifier may display a dust filter usage time (operation time) and display the remained residual usage time of the filter. The dust filter is based on an ultra-fine filter, in which a super-ultra-fine mini filter, a super-ultra-fine plus filter, and a smoke deodorizing filter may be inserted.

The air purifier may largely include a pre-filter for filtering living dust in the air, a deodorizing filter for removing odors in the air, and a HEPA filter for removing fine dust. The fine dust may be filtered through a HEPA filter, which is a special fiber filter used in semiconductor clean room, and has excellent adsorption power and accordingly, filters out fine dust.

The class of the air purifier filter is classified into E (10, 11, 12) to H (13, 14) and U (15, 16, 17) and H13 and H14 are called a HEPA filter. The higher the last number, the higher the probability of filtering out 0.3 μm dust particle, which may be replaced with a new filter according to the amount of the filter used. Since the capability to purify the fine dust is different according to the type of the filter, an artificial intelligence model learner 124 of the contaminated air exposure level inferring apparatus 100 or the server 300 may consider the amount of the filter used according to the purification capability of the type of the filter when learning the artificial intelligence model.

The portable air purifier may control home electronics and receive various additional information through a Smart ThinQ app, which is a product of the applicant company, through an IoT technology. In addition, the filter replacement time may be confirmed through the app.

Since the data on the intensity of the fan or the amount of the filter used of the portable air purifier 110 operated by the user during holding may be a basis for inferring the amount of air purified while the user operates the portable air purifier, it may be used as a label value for learning the artificial intelligence model.

In an embodiment of the present disclosure, the fan speed of the portable air purifier 110 may be adjusted automatically and at three levels of strong wind to weak wind according to the indoor air condition. The portable air purifier 110 may be set automatically because the air quality due to fine dust is monitored in real time by an app.

For example, in a state where the portable air purifier 110 has been set to the automatic mode, when the fine dust concentration is high, the intensity of the fan of the portable air purifier will be strong and the amount of the filter used will be increased, thereby increasing the contaminated air exposure level of the user. Conversely, when the fine dust concentration is low, the intensity of the fan of the portable air purifier will be weak and the amount of the filter used will be low, thereby reducing the contaminated air exposure level of the user. In addition, when the fine dust concentration is low, the user may manually stop the operation of the portable air purifier 110. As described above, when the amount of filter used is high considering the fine dust concentration and the amount of the filter used of the portable air purifier 110, the intensity of the fan of the air purifier, etc., a reference may be quantitatively determined as to whether the contaminated air exposure level of the user is high, medium, or low. The contaminated air exposure level of the user may be machine-learned by collecting the usage history of the portable air purifier to infer the contaminated air exposure level of the user according to the fine dust concentration and the amount of the filter used.

In an embodiment of the present disclosure, when the user has operated the portable air purifier 110 for 1 hour by setting the wind intensity of the portable air purifier to 'weak' in the range of the fine dust concentration 'normal' to be changed to 'good,' the contaminated air exposure level of the user is classified as 'good,' when the user has operated the portable air purifier 110 for 1 hour by setting the intensity of the fan of the portable air purifier to 'strong' in the range of the fine dust concentration 'bad' to be changed to 'good,' the contaminated air exposure level of the user may be classified into 'normal,' when the user has operated the portable air purifier 110 for 1 hour by setting the wind intensity of the portable air purifier to 'strong' in the range of the fine dust concentration 'bad' to be changed to 'normal,' the contaminated air exposure level of the user may be classified into 'high,' and when the fine dust concentration is maintained as 'bad' even if the user has operated the portable air purifier 110 for 1 hour by setting the wind intensity of the portable air purifier to 'strong' in the range of the fine dust concentration 'bad,' the contaminated air exposure level of the user may be classified into 'very high.' In an embodiment of the present disclosure, the contaminated air exposure level may be determined experimentally by the change trend of the fine dust concentration. In another embodiment of the present disclosure, the contaminated air exposure level may be determined by analyzing the relationship between the change trend of the current fine dust concentration, the intensity of the fan and the amount of the filter used of the portable air purifier.

In the present disclosure, the contaminated air exposure level may be determined by using data analysis tools such as a decision tree. The contaminated air exposure level may be classified through the decision tree analysis for classification and regression analysis with respect to the data on the fine dust concentration, the amount of the filter used, and the intensity of the fan of the portable air purifier 110 received from the data receiver of the contaminated air exposure level inferring apparatus 100. A Classification And Regression Tree (CART) algorithm may be used for decision tree analysis.

Figure 4:
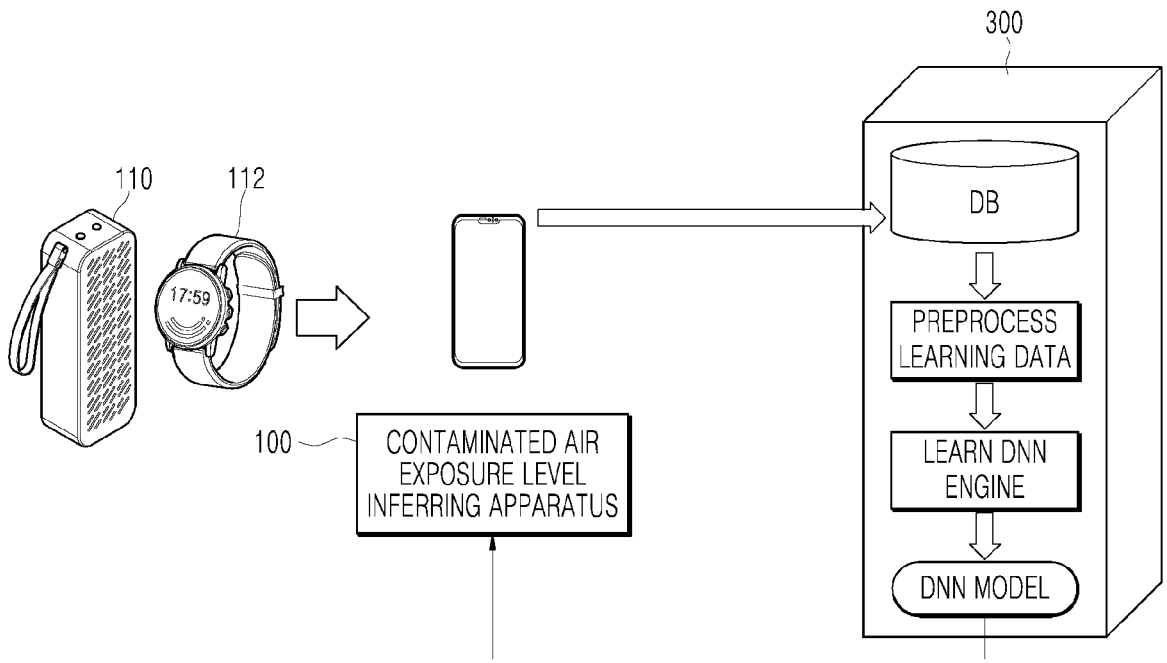
FIG. 4 is an exemplary diagram of the contaminated air exposure level inferring system including the contaminated air exposure level inferring apparatus and the server.

FIG. 4 is an exemplary diagram of a contaminated air exposure level inferring system including the contaminated air exposure level inferring apparatus and the server.

The contaminated air exposure level inferring apparatus 100 and the server 300 may be equipped with an artificial neural network for learning an artificial intelligence model. In addition, the contaminated air exposure level inferring apparatus 100 may transmit information on the contaminated air exposure level or the optimal course execution instruction according to the contaminated air exposure level inferred through the learned artificial intelligence model to the external home appliances 200 such as the searched one or more clothing and air purification-related home appliances.

The contaminated air exposure level inferring apparatus 100 may be used to learn the artificial intelligence model for inferring (classifying) the contaminated air exposure level of the user. For example, the contaminated air exposure level inferring apparatus 100 may include the artificial intelligence model learner 124, and may directly generate by itself and also use the learned artificial intelligence model in order to classify the contaminated air exposure level, but the server 300 may also include the artificial intelligence model learner, and use data in the form of big data collected by the server 300 instead.

The contaminated air exposure level inferring apparatus 100 may use various programs related to an artificial intelligence algorithm stored in a local area or stored in the server 300. That is, the server 300 may serve to learn the artificial intelligence model by using data collected together with data collection. The contaminated air exposure level inferring apparatus 100 may classify the contaminated air exposure level based on the generated artificial intelligence model.

The server 300 may receive the air contamination level, in particular, the data on the fine dust concentration and the data on the amount of the filter used of the portable air purifier 110 obtained by the portable air purifier 110 or the wearable device 112 from the contaminated air exposure level inferring apparatus 100. The server 300 may provide the training data necessary for classifying the contaminated air exposure level of the user by using the artificial intelligence algorithm and various programs related to the artificial intelligence algorithm, for example, an API, a workflow, etc. to the contaminated air exposure level inferring apparatus 100 or the user terminal including the contaminated air exposure level inferring apparatus 100. The server 300 may learn the artificial intelligence model by using the training data including the air contamination level for classifying the contaminated air exposure level, in particular, the data on the fine dust concentration and the data on the amount of the filter used of the portable air purifier 110. In addition, the server 300 may evaluate the artificial intelligence model, and update the artificial intelligence model for better performance even after the evaluation. Here, the contaminated air exposure level inferring apparatus 100 may perform a series of operations performed by the server 300 alone or together with the server 300.

The server 300 may include an artificial intelligence model learner for generating the artificial intelligence model that has learned the collected contaminated air exposure level of the user through a deep neural network (DNN). The artificial intelligence model learner of the server may be configured to extract the learning data necessary for learning through the deep neural network (DNN) from a database for storing data necessary for inferring the contaminated air exposure level for machine learning or deep learning, to preprocess the learning data in order to increase the accuracy of the learning data, to learn the learning data through the deep neural network (DNN), and to generate the learned artificial intelligence model.

Data preprocessing refers to removing or modifying the learning data to maximally increase the accuracy of source data. In addition, if they contain excessively insignificant data, it also reduces and adjusts them properly to change into a form that is easy to manage and use. The data preprocessing includes data refinement, data integration, data transformation, data reduction, etc. The data refinement is to fill missing values, to smooth noisy data, to identify outliers, and to calibrate data inconsistency.

The server 300 may be configured to transmit the learned artificial intelligence model that has learned through the artificial intelligence model learner to the contaminated air exposure level inferring apparatus 100. The exposure level classifier 126 of the contaminated air exposure level inferring apparatus 100 may be configured to classify the contaminated air exposure level through the learned artificial intelligence model received from the server.

Figure 5:
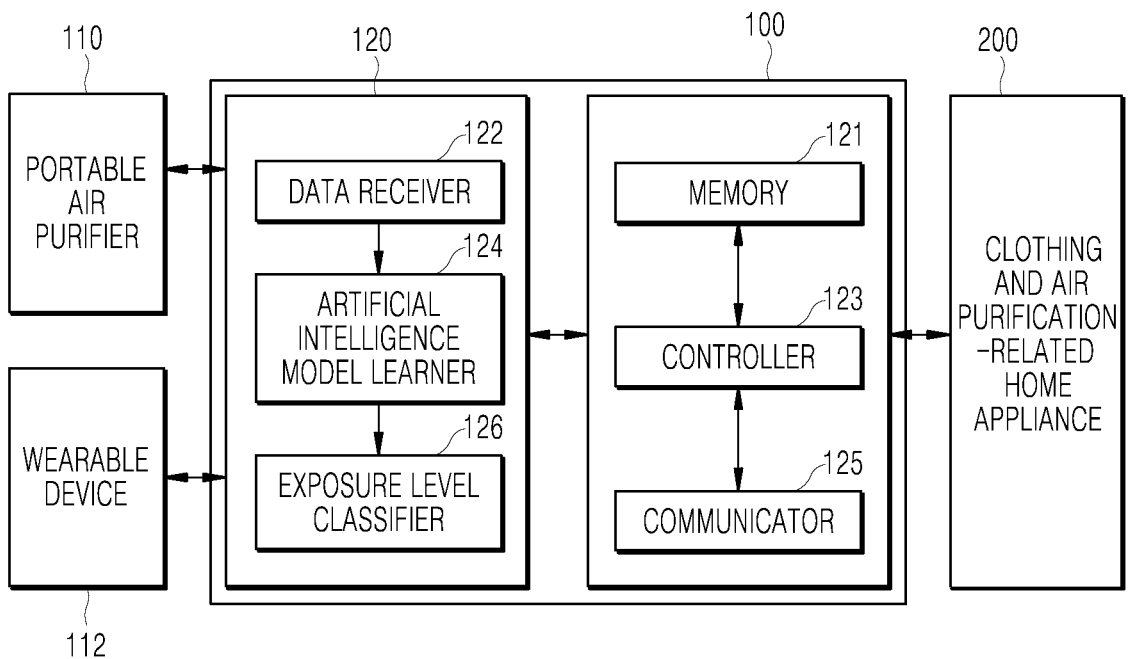
FIG. 5 is a block diagram of the contaminated air exposure level inferring apparatus according to an embodiment of the present disclosure.

FIG. 5 is a block diagram of the contaminated air exposure level inferring apparatus according to an embodiment of the present disclosure.

The contaminated air exposure level inferring apparatus 100 may include a contaminated air exposure level inferrer 120, the memory 121, a controller 123, and the communicator 125. The contaminated air exposure level inferrer 120 may include the data receiver 122, the artificial intelligence model learner 124, and the exposure level classifier 126. The data receiver 122 may receive an air contamination level, in particular, a concentration related to fine dust, from the portable air purifier 110 and the wearable device 112. The data receiver 122 may receive the data on the amount of the filter used from the portable air purifier 110. In addition, the data receiver 122 may receive other data necessary for inferring an air contamination level, for example, ozone ($O_3$), yellow dust, nitrogen dioxide ($NO_2$), carbon monoxide (CO), and sulfur dioxide ($SO_2$).

In addition, the controller 123 may control the memory 121 capable of storing various data and the communicator 125 capable of communicating with an external home appliance, and control components necessary for inferring the contaminated air exposure level in the contaminated air exposure level inferring apparatus 100. The controller 123 may infer the information on the contamination air exposure level and generate a control signal having protocol information for the external home appliance 200 such as clothing and air purification-related home appliances to be communicated with respect to the inferred result. The communicator 125 may transfer the generated control signal to the interlocked external home appliance 200 such as clothing and air purification-related home appliances. In another embodiment of the present disclosure, the communicator 125 may notify the user when the inferred contaminated air exposure level or the measured fine dust concentration exceeds a predetermined threshold. In another embodiment of the present disclosure, the communicator 125 may notify the user of at least one among the information of the fine dust sensor, the dust improvement effect by the air purification of the portable air purifier, or the contamination air exposure level per hour.

The contaminated air exposure level inferrer 120 may infer the contaminated air exposure level based on at least one among a fine dust concentration per a specific hour necessary for the artificial intelligence model learning, the intensity of the fan of the portable air purifier, and the amount of the filter used of the portable air purifier.

The artificial intelligence model learner 124 of the contaminated air exposure level inferrer 120 may learn the artificial intelligence model based on the data received from at least one of the portable air purifier 110 or the wearable device 112. For this purpose, the contaminated air exposure level inferrer 120 may include the data receiver 122 for collecting the data on the air contamination level from at least one of the portable air purifier 110 or the wearable device 112, the artificial intelligence model learner 124 for learning through learning data including the data on the air contamination level and the data matching a label of the contamination air exposure level to the data on the air contamination level, and learning an exposure level classifying engine so as to classify and output the contaminated air exposure level, and the exposure level classifier 126 for classifying and outputting the contaminated air exposure level through the exposure level classifying engine based on the data received from the portable air purifier 110 and the wearable device 112. The contaminated air exposure level information output from the exposure level classifier 126 may be sent to the external home appliances 200 such as clothing and air purification-related home appliances through the communicator 125.

In another embodiment of the present disclosure, as described in FIG. 4, the contaminated air exposure level inferrer 120 may use the server 300 for the purpose of learning the artificial intelligence model for inferring (or classifying) the contaminated air exposure level of the user. The server 300 may receive the information on the fine dust concentration, and the intensity of the fan and the amount of the filter used of the portable air purifier 110 received from the portable air purifier 110 and the wearable device 112. The server 300 may be configured to transmit the learned artificial intelligence model that has learned through the artificial intelligence model learner to the contaminated air exposure level inferring apparatus 100. The exposure level classifier 126 of the contaminated air exposure level inferring apparatus 100 may be configured to infer the contaminated air exposure level through the learned artificial intelligence model received from the server 300.

The controller 123 of the contaminated air exposure level inferring apparatus 100 may include all kinds of devices capable of processing data such as a processor, for example, an MCU. Here, 'the processor' may, for example, refer to a data processing device embedded in hardware, which has physically structured circuitry to perform a function represented by codes or instructions contained in a program. As one example of the data processing device embedded in the hardware, a microprocessor, a central processing unit (CPU), a processor core, a multiprocessor, an application-specific integrated circuit (ASIC), a field programmable gate array (FPGA), and the like may be included, but the scope of the present disclosure is not limited thereto.

The communicator 125 of the contaminated air exposure level inferring apparatus 100 may provide a communication interface necessary for providing a transmission and reception signal between the external home appliance 200 such as clothing and air purification-related home appliance, and/or the server 300 in the form of packet data in interlock with the network 400. Furthermore, the communicator 125 may support various kinds of object-to-object intelligent communication (such as Internet of things (IoT), Internet of everything (IoE), and Internet of small things (IoST)), and may support communication such as machine to machine (M2M) communication, vehicle to everything (V2X) communication, and device to device (D2D) communication.

Figure 6:
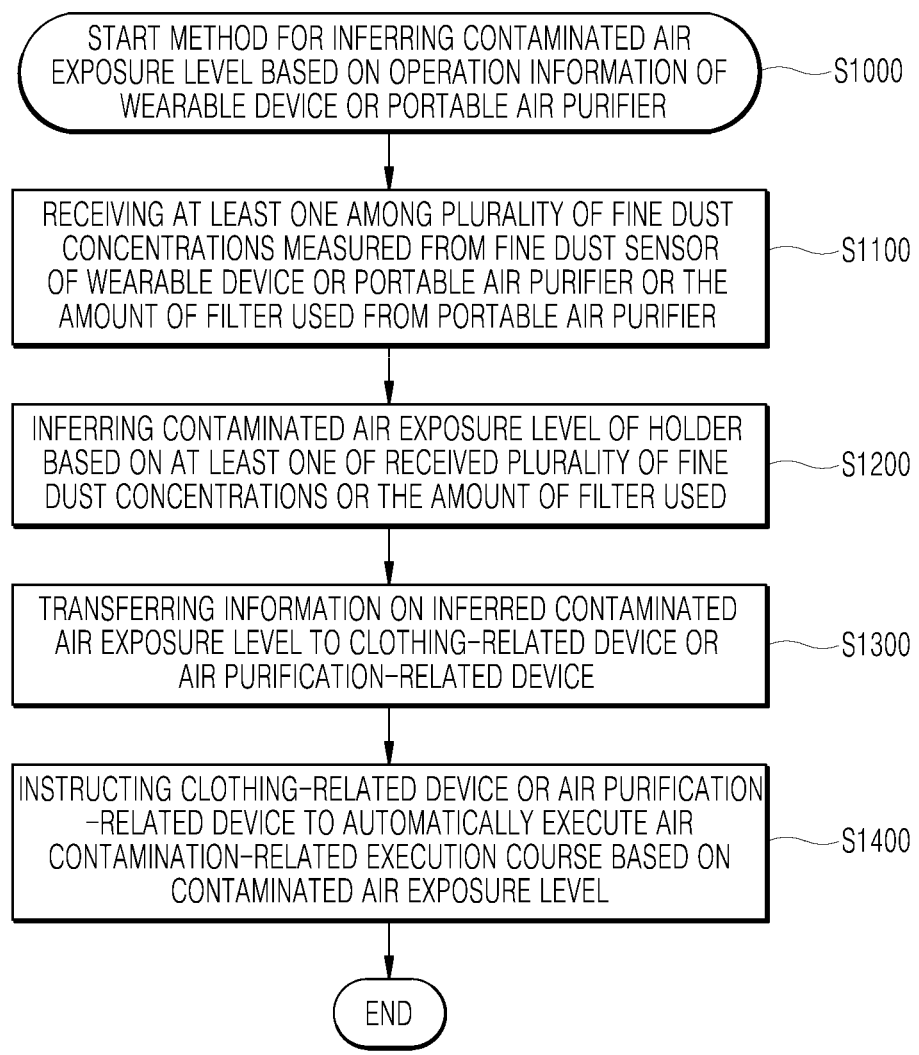
FIG. 6 is a flowchart showing a contaminated air exposure level inferring method according to an embodiment of the present disclosure.

FIG. 6 is a flowchart showing a contaminated air exposure level inferring method according to an embodiment of the present disclosure.

The contaminated air exposure level inferring apparatus 100 may be turned on together with the portable air purifier 110 or the wearable device 112 when the power is turned on, may be turned on by a user setting, and a contaminated air exposure level inferring process is started. (operation S1000).

The contaminated air exposure level inferring apparatus 100 may receive at least one of the fine dust concentration measured per a specific time from the fine dust sensor of the wearable device 112 or the portable air purifier 110 or the amount of the filter used of the portable air purifier 110 (operation S1100). In addition, the contaminated air exposure level inferring apparatus 100 may collect data on the intensity of the fan of the portable air purifier 110 operated by the user during holding. The data on the intensity of the fan or the amount of the filter used of the portable air purifier 110 operated by the user during holding may be used as a label value for learning the artificial intelligence model.

The contaminated air exposure level inferrer 120 may infer the contaminated air exposure level of the user based on at least one of the received fine dust concentration or the amount of the filter used (operation S1200).

The contaminated air exposure level inferring apparatus 100 may transfer the information on the contaminated air exposure level inferred through the communicator 125 to the external home appliance 200 such as clothing and air purification-related home appliance (operation S1300). In another embodiment of the present disclosure, the contaminated air exposure level inferring apparatus 100 may transfer the information on the inferred contaminated air exposure level through the communicator 125 to the external home appliance 200 such as clothing and air purification-related home appliance when the inferred contaminated air exposure level of the user exceeds a predetermined threshold. In addition, when the inferred contaminated air exposure level of the user exceeds the predetermined threshold, whether to wear a mask may be notified of the user. The predetermined threshold may be determined according to the contaminated air exposure level considering the fine dust concentration. For example, the user may be notified of wearing the mask when the fine dust concentration is bad or the contaminated air exposure level is high. The contaminated air exposure level inferring apparatus 100 may notify the user of a mask detachment when a change in the fine dust concentration occurs at the time of moving to a specific place such as entering or exiting a building of the user, or entering a subway station.

The contaminated air exposure level inferring apparatus 100 may instruct the clothing-related device or the air purification-related device to automatically execute an air contamination-related execution course based on the contaminated air exposure level (operation S1400).

When the contaminated air exposure level or the automatic execution instruction of the air contamination-related execution course is transmitted to the external home appliance 200 such as the clothing and air purification-related home appliance, the contaminated air exposure level inferring process is terminated.

In another embodiment of the present disclosure, a program programmed to execute the contaminated air exposure level inferring process may be stored in a computer-readable recording medium.

Figure 7A:
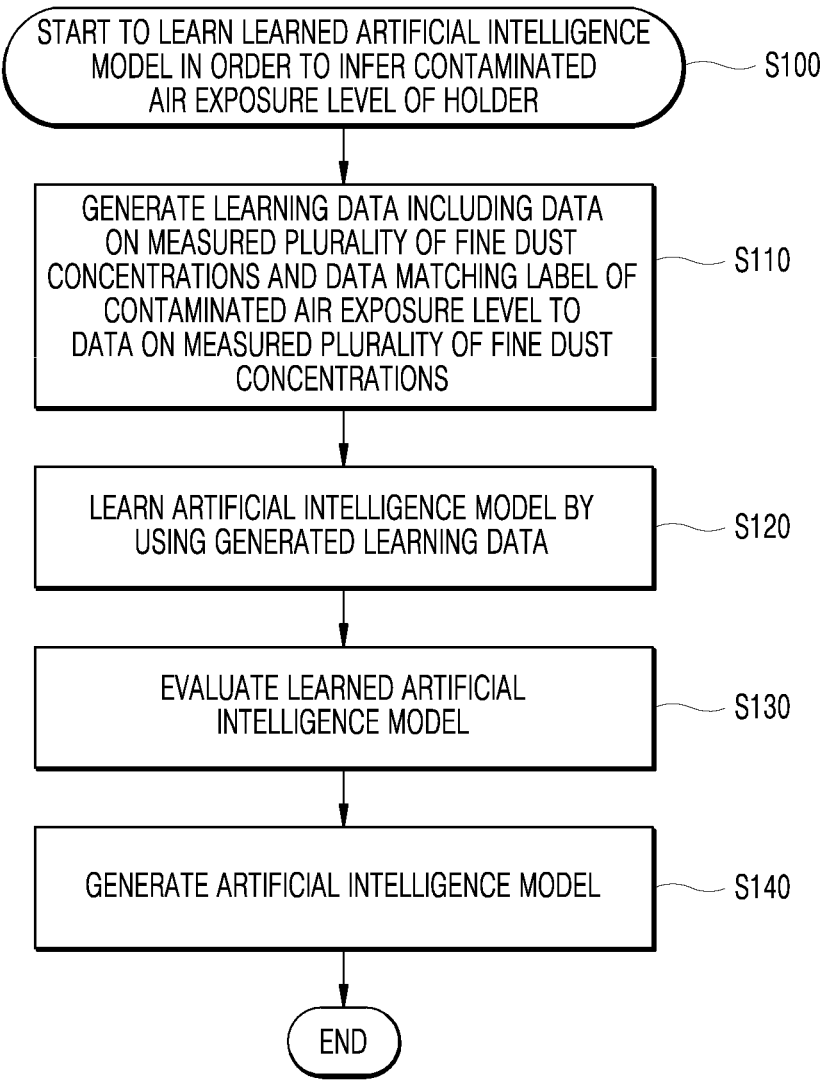
FIG. 7A is a flowchart learning an exposure level classifying engine through an artificial intelligence model learner according to an embodiment of the present disclosure.

FIG. 7A is a flowchart for learning the exposure level classifying engine through the artificial intelligence model learner according to an embodiment of the present disclosure.

The operation S1200 of FIG. 6 may be executed through the artificial intelligence model for inferring the contaminated air exposure level. Learning of the artificial intelligence model for inferring the contaminated air exposure level to be applied to the contaminated air exposure level inferring apparatus 100 is started (operation S100).

Learning data for the artificial intelligence model including data on a plurality of fine dust concentrations and data matching a label of the contaminated air exposure level to the data on the plurality of the fine dust concentration may be generated (operation S110). In another embodiment, the artificial intelligence learning data including the data on the plurality of fine dust concentrations and the amount of the filter used after the portable air purifier is operated, and the data matching the label of the contaminated air exposure level to the amount of the filter used and test data may be generated. Since the data on the amount of the filter used is the amount of the filter used that has been used to purify the exposed contaminated air by the user holding the portable air purifier 110, the contaminated air exposure level of the user may be evaluated by the amount of the filter used. Accordingly, it is possible to generate features of the data on the plurality of fine dust concentrations and the amount of the filter used after the portable air purifier is operated, and the data matching the label of the contaminated air exposure level to the data on the amount of the filter used.

A ratio of the learning data and the test data may vary according to the amount of data, and may be generally defined as a ratio of 7:3. The collecting and storing the learning data may be performed by the data receiver 122 of the contaminated air exposure level inferring apparatus 100 or the server 300. The learning data for the artificial intelligence model may be subjected to data preprocessing and data augmentation in order to obtain accurate learning results.

The artificial intelligence algorithm such as machine learning or deep neural network (DNN) may learn the features of the contaminated air exposure level of the user by using the learning data collected through supervised learning (operation S120). The artificial intelligence model learner 124 may infer the contamination air exposure level by performing classification or regression analysis based on the artificial intelligence by using the received air contamination level, in particular, the data on the fine dust. The classification analysis may execute through the learning data including at least one data among the fine dust concentration per a specific time, the intensity of the fan and the amount of the filter used of the portable air purifier 110, and the labeled data of the contaminated air exposure level based on the amount of purification considering the intensity of the fan or the amount of the filter used. The regression analysis may be executed to predict future contaminated air exposure level to notify the user of whether to wear a mask in advance considering the fine dust concentration, the amount of the filter used, etc.

In an embodiment of the present disclosure, a deep learning based screen analyzer may be used, and for example, the artificial intelligence learning model may be tuned and used based on TensorFlow or Keras, which is an artificial intelligence language library used for artificial intelligence programming.

The artificial intelligence model is generated through evaluation of the learned artificial intelligence model (operation S130) (operation S140). The evaluation of the learned artificial intelligence model (operation S130) is performed by using the test data. Throughout the present disclosure, the 'learned artificial intelligence model' means learning the learning data and deciding the learned model after testing through the test data even without special mention.

Figure 7B:
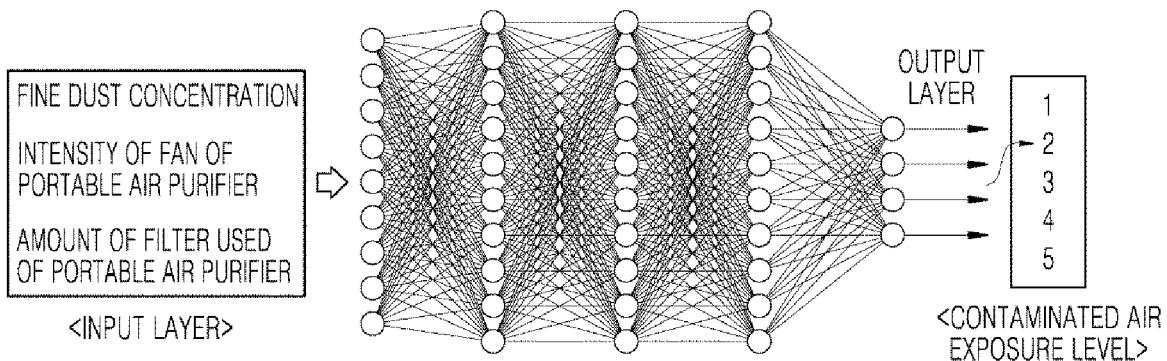
FIG. 7B is a diagram for explaining a structure of an artificial intelligence model learned to infer a contaminated air exposure level in the contaminated air exposure level inferring apparatus or the server according to an embodiment of the present disclosure.

FIG. 7B is a diagram for explaining a structure of the artificial intelligence model learning to infer the contaminated air exposure level in the contaminated air exposure level inferring apparatus or the server according to an embodiment of the present disclosure.

The artificial intelligence (AI) is one field of computer science and information technology that studies methods to make computers mimic intelligent human behaviors such as reasoning, learning, self-improving and the like.

In addition, the artificial intelligence does not exist on its own, but is rather directly or indirectly-related to a number of other fields in computer science. In recent years, there have been numerous attempts to introduce an element of AI into various fields of information technology to solve problems in the respective fields.

Machine learning is an area of artificial intelligence that includes the field of study that gives computers the capability to learn without being explicitly programmed.

More specifically, machine learning is a technology that investigates and builds systems, and algorithms for such systems, which are capable of learning, making predictions, and enhancing their own performance on the basis of experiential data. Machine learning algorithms, rather than only executing rigidly set static program commands, may take an approach that builds models for deriving predictions and decisions from inputted data.

Many Machine Learning algorithms have been developed on how to classify data in the Machine Learning. Representative examples of such machine learning algorithms for data classification include a decision tree, a Bayesian network, a support vector machine (operation SVM), an artificial neural network (ANN), and so forth.

Decision tree refers to an analysis method that uses a tree-like graph or model of decision rules to perform classification and prediction.

Bayesian network may include a model that represents the probabilistic relationship (conditional independence) among a set of variables. Bayesian network may be appropriate for data mining via unsupervised learning.

SVM may include a supervised learning model for pattern detection and data analysis, heavily used in classification and regression analysis.

ANN is a data processing system modeled after the mechanism of biological neurons and interneuron connections, in which a number of neurons, referred to as nodes or processing elements, are interconnected in layers.

ANNs are models used in machine learning and may include statistical learning algorithms conceived from biological neural networks (particularly of the brain in the central nervous system of an animal) in machine learning and cognitive science.

ANNs may refer generally to models that have artificial neurons (nodes) forming a network through synaptic interconnections, and acquires problem-solving capability as the strengths of synaptic interconnections are adjusted throughout training.

The terms 'artificial neural network' and 'neural network' may be used interchangeably herein.

An ANN may include a number of layers, each including a number of neurons. In addition, the Artificial Neural Network may include the synapse for connecting between neuron and neuron.

An ANN may be defined by the following three factors: (1) a connection pattern between neurons on different layers; (2) a learning process that updates synaptic weights; and (3) an activation function generating an output value from a weighted sum of inputs received from a lower layer.

The Artificial Neural Network may include network models of the method such as Deep Neural Network (DNN), Recurrent Neural Network (RNN), Bidirectional Recurrent Deep Neural Network (BRDNN), Multilayer Perceptron (MLP), and Convolutional Neural Network (CNN), but is not limited thereto.

The terms "layer" and "hierarchy" may be used interchangeably herein.

An ANN may be classified as a single-layer neural network or a multi-layer neural network, based on the number of layers therein.

In general, a single-layer neural network may include an input layer and an output layer.

In addition, a general Multi-Layer Neural Network is composed of an Input layer, one or more Hidden layers, and an Output layer.

The Input layer is a layer that accepts external data, the number of neurons in the Input layer is equal to the number of input variables, and the Hidden layer is disposed between the Input layer and the Output layer and receives a signal from the Input layer to extract the characteristics to transfer it to the Output layer. The output layer receives a signal from the hidden layer and outputs an output value based on the received signal. The Input signal between neurons is multiplied by each connection strength (weight) and then summed, and if the sum is larger than the threshold of the neuron, the neuron is activated to output the output value obtained through the activation function.

Meanwhile, the Deep Neural Network including a plurality of Hidden layers between the Input layer and the Output layer may be a representative Artificial Neural Network that implements Deep Learning, which is a type of Machine Learning technology.

The Artificial Neural Network may be trained by using training data. Here, the training may refer to the process of determining parameters of the artificial neural network by using the training data, to perform tasks such as classification, regression analysis, and clustering of inputted data. Such parameters of the artificial neural network may include synaptic weights and biases applied to neurons.

An artificial neural network trained using training data may classify or cluster inputted data according to a pattern within the inputted data.

Throughout the present specification, an artificial neural network trained using training data may be referred to as a trained model.

Hereinbelow, learning paradigms of an artificial neural network will be described in detail.

The learning method of the Artificial Neural Network may be largely classified into Supervised Learning, Unsupervised Learning, Semi-supervised Learning, and Reinforcement Learning.

The Supervised Learning is a method of the Machine Learning for inferring one function from the training data.

Then, among the thus inferred functions, outputting consecutive values is referred to as regression, and predicting and outputting a class of an input vector is referred to as classification.

In the Supervised Learning, the Artificial Neural Network is learned in a state where a label for the training data has been given.

Here, the label may refer to a target answer (or a result value) to be guessed by the artificial neural network when the training data is inputted to the artificial neural network.

Throughout the present specification, the target answer (or a result value) to be guessed by the artificial neural network when the training data is inputted may be referred to as a label or labeling data.

Throughout the present specification, assigning one or more labels to training data in order to train an artificial neural network may be referred to as labeling the training data with labeling data.

Training data and labels corresponding to the training data together may form a single training set, and as such, they may be inputted to an artificial neural network as a training set.

The training data may exhibit a number of features, and the training data being labeled with the labels may be interpreted as the features exhibited by the training data being labeled with the labels. In this case, the training data may represent a feature of an input object as a vector.

Using training data and labeling data together, the artificial neural network may derive a correlation function between the training data and the labeling data. Then, the parameter of the Artificial Neural Network may be determined (optimized) by evaluating the function inferred from the Artificial Neural Network.

Unsupervised learning is a machine learning method that learns from training data that has not been given a label.

More specifically, unsupervised learning may be a training scheme that trains an artificial neural network to discover a pattern within given training data and perform classification by using the discovered pattern, rather than by using a correlation between given training data and labels corresponding to the given training data.

Examples of unsupervised learning include, but are not limited to, clustering and independent component analysis.

Examples of artificial neural networks using unsupervised learning include, but are not limited to, a generative adversarial network (GAN) and an autoencoder (AE).

GAN is a machine learning method in which two different artificial intelligences, a generator and a discriminator, improve performance through competing with each other.

The generator may be a model generating new data that generates new data based on true data.

The discriminator may be a model recognizing patterns in data that determines whether inputted data is from the true data or from the new data generated by the generator.

Furthermore, the generator may receive and learn from data that has failed to fool the discriminator, while the discriminator may receive and learn from data that has succeeded in fooling the discriminator. Accordingly, the generator may evolve so as to fool the discriminator as effectively as possible, while the discriminator evolves so as to distinguish, as effectively as possible, between the true data and the data generated by the generator.

An auto-encoder (AE) is a neural network which aims to reconstruct its input as output.

More specifically, AE may include an input layer, at least one hidden layer, and an output layer.

Since the number of nodes in the hidden layer is smaller than the number of nodes in the input layer, the dimensionality of data is reduced, thus leading to data compression or encoding.

Furthermore, the data outputted from the hidden layer may be inputted to the output layer. Given that the number of nodes in the output layer is greater than the number of nodes in the hidden layer, the dimensionality of the data increases, thus leading to data decompression or decoding.

Furthermore, in the AE, the inputted data is represented as hidden layer data as interneuron connection strengths are adjusted through training. The fact that when representing information, the hidden layer is able to reconstruct the inputted data as output by using fewer neurons than the input layer may indicate that the hidden layer has discovered a hidden pattern in the inputted data and is using the discovered hidden pattern to represent the information.

Semi-supervised learning is machine learning method that makes use of both labeled training data and unlabeled training data.

One of semi-supervised learning techniques involves guessing the label of unlabeled training data, and then using this guessed label for learning. This technique may be used advantageously when the cost associated with the labeling process is high.

Reinforcement learning may be based on a theory that given the condition under which a reinforcement learning agent may determine what action to choose at each time instance, the agent may find an optimal path to a solution solely based on experience without reference to data.

The Reinforcement Learning may be mainly performed by a Markov Decision Process (MDP).

Markov decision process consists of four stages: first, an agent is given a condition containing information required for performing a next action; second, how the agent behaves in the condition is defined; third, which actions the agent should choose to get rewards and which actions to choose to get penalties are defined; and fourth, the agent iterates until future reward is maximized, thereby deriving an optimal policy.

An artificial neural network is characterized by features of its model, the features including an activation function, a loss function or cost function, a learning algorithm, an optimization algorithm, and so forth. Also, the hyperparameters are set before learning, and model parameters may be set through learning to specify the architecture of the artificial neural network.

For instance, the structure of an artificial neural network may be determined by a number of factors, including the number of hidden layers, the number of hidden nodes included in each hidden layer, input feature vectors, target feature vectors, and so forth.

Hyperparameters may include various parameters which need to be initially set for learning, much like the initial values of model parameters. Also, the model parameters may include various parameters sought to be determined through learning.

For instance, the hyperparameters may include initial values of weights and biases between nodes, mini-batch size, iteration number, learning rate, and so forth. Furthermore, the model parameters may include a weight between nodes, a bias between nodes, and so forth.

Loss function may be used as an index (reference) in determining an optimal model parameter during the learning process of an artificial neural network. Learning in the artificial neural network involves a process of adjusting model parameters so as to reduce the loss function, and the purpose of learning may be to determine the model parameters that minimize the loss function.

Loss functions typically use means squared error (MSE) or cross entropy error (CEE), but the present disclosure is not limited thereto.

Cross-entropy error may be used when a true label is one-hot encoded. One-hot encoding may include an encoding method in which among given neurons, only those corresponding to a target answer are given 1 as a true label value, while those neurons that do not correspond to the target answer are given 0 as a true label value.

In machine learning or deep learning, learning optimization algorithms may be deployed to minimize a cost function, and examples of such learning optimization algorithms include gradient descent (GD), stochastic gradient descent (operation SGD), momentum, Nesterov accelerate gradient (NAG), Adagrad, AdaDelta, RMSProp, Adam, and Nadam.

GD includes a method that adjusts model parameters in a direction that decreases the output of a cost function by using a current slope of the cost function.

The direction in which the model parameters are to be adjusted may be referred to as a step direction, and a size by which the model parameters are to be adjusted may be referred to as a step size.

Here, the step size may mean a learning rate.

GD obtains a slope of the cost function through use of partial differential equations, using each of model parameters, and updates the model parameters by adjusting the model parameters by a learning rate in the direction of the slope.

SGD may include a method that separates the training dataset into mini batches, and by performing gradient descent for each of these mini batches, increases the frequency of gradient descent.

Adagrad, AdaDelta and RMSProp may include methods that increase optimization accuracy in SGD by adjusting the step size, and may also include methods that increase optimization accuracy in SGD by adjusting the momentum and step direction. Adam may include a method that combines momentum and RMSProp and increases optimization accuracy in SGD by adjusting the step size and step direction. Nadam may include a method that combines NAG and RMSProp and increases optimization accuracy by adjusting the step size and step direction.

Learning rate and accuracy of an artificial neural network rely not only on the structure and learning optimization algorithms of the artificial neural network but also on the hyperparameters thereof. Accordingly, in order to obtain a good learning model, it is important to choose a proper structure and learning algorithms for the artificial neural network, but also to choose proper hyperparameters.

In general, the artificial neural network is first trained by experimentally setting hyperparameters to various values, and based on the results of training, the hyperparameters may be set to optimal values that provide a stable learning rate and accuracy.

Learning of the artificial intelligence model for inferring the contaminated air exposure level of the user may be performed in any one form of supervised learning, unsupervised learning, and reinforcement learning.

In an embodiment of the present disclosure, the artificial intelligence model may be learned through classification analysis of machine learning. Supervised learning may be performed by using the artificial intelligence model learning data including features of the data on the plurality of fine dust concentrations and the data matching the label of the contaminated air exposure level to the data on the plurality of fine dust concentrations. In another embodiment, the supervised learning may be performed by using the artificial intelligence learning data including the features of the data on the plurality of fine dust concentrations and the amount of the filter used after the portable air purifier is operated, and the data matching the label of the contaminated air exposure level to the amount of the filter used.

In an embodiment of the present disclosure, the structure of the artificial intelligence model may be composed of the fine dust concentration, the intensity of the fan of the portable air purifier, and the amount of the filter used of the portable air purifier as an input layer, four hidden layers, and the contaminated air exposure level of the user as five output layers of Level 1: very low, Level 2: low, Level 3: normal, Level 4: high, Level 5: very high. In another embodiment of the present disclosure, the structure of the artificial intelligence model may be composed of at least one input layer among the fine dust concentration, the intensity of the fan of the portable air purifier, or the amount of the filter used of the portable air purifier, a plurality of hidden layers, and four output layers of good (very low, low), normal, high, very high.

Figure 8:
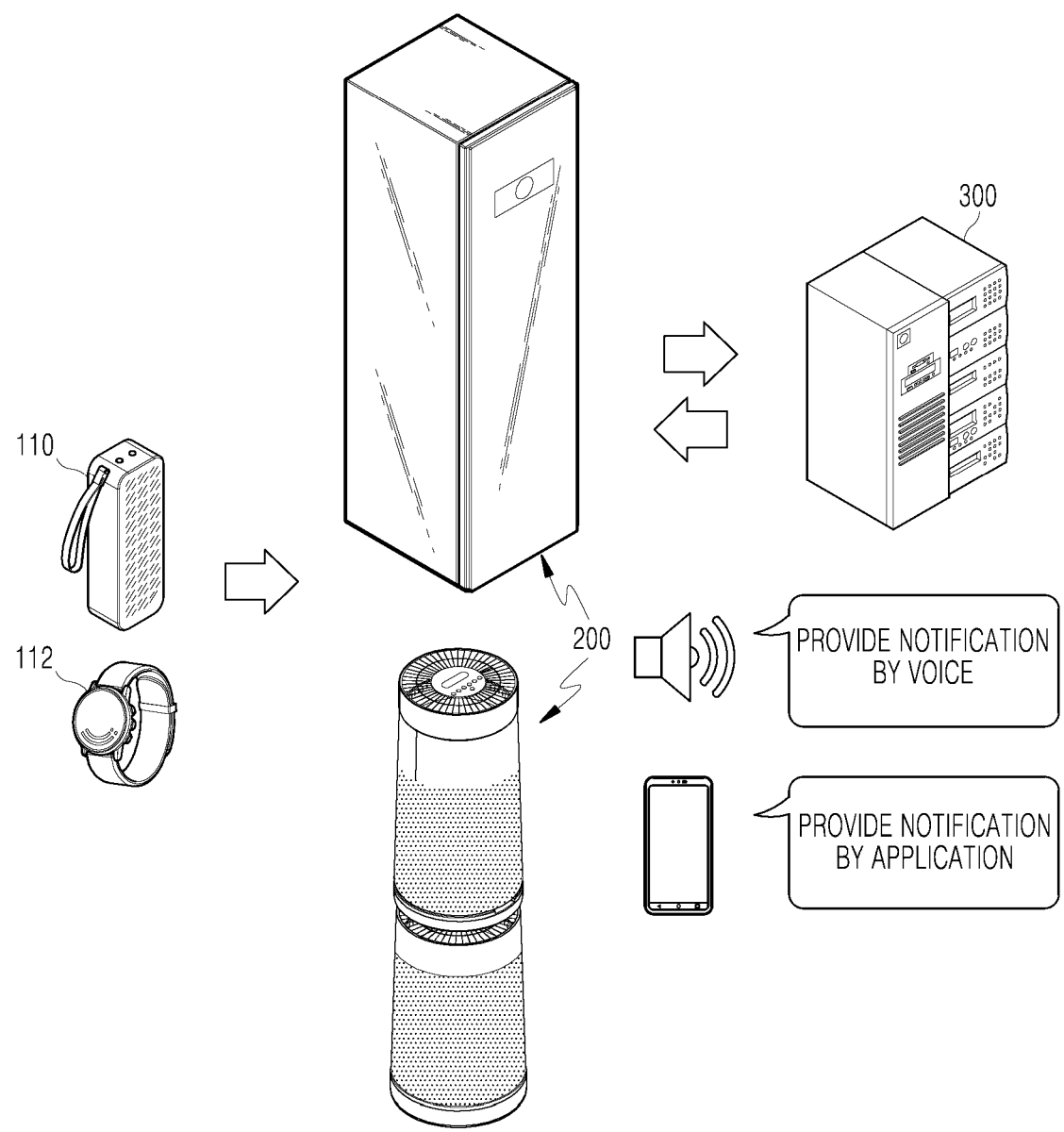
FIG. 8 is an exemplary diagram notifying a user of the contaminated air exposure level inferred through the contaminated air exposure level inferring apparatus according to an embodiment of the present disclosure.

FIG. 8 is an exemplary diagram for notifying a user of the inferred contaminated air exposure level through the contaminated air exposure level inferring apparatus according to an embodiment of the present disclosure.

The external home appliance 200 such as clothing and air purification-related home appliance, which is interlocked with the portable air purifier 110 or the wearable device 112 to receive the information on the contamination air exposure level may notify the user of at least one among the information of the fine dust sensor, the dust improvement effect by the air purification of the portable air purifier, or the contamination air exposure level per the specific time.

The interlocked external home appliance 200 such as clothing and air purification-related home appliance may instruct to automatically execute a fine dust-related optimal course so as to match the inferred contaminated air exposure level result to the external home appliance 200 such as clothing and air purification-related home appliance. When the information on the contamination air exposure level is received in the interlocked external home appliance 200 such as the clothing and the air purification-related home appliance from the contaminated air exposure level inferring apparatus 100, the external home appliance 200 such as the clothing and the air purification-related home appliance may implement an air contamination-related course.

Regarding the information on the contaminated air exposure level, the contaminated air exposure level inferring apparatus 100 or the external home appliance 200 such as clothing and air purification-related home appliance may provide a notification function through voice or an application. For example, when the contamination air exposure level is high, the clothing manager 201 may execute a fine dust course among the clothing management courses. The washing machine 202 may select a steam cleaning course among the washing courses. In addition, since the user has been exposed to fine dust, the air purifier 203 may be automatically operated by sensing the dust level.

The received contaminated air exposure level information may update usage information in the data storage device or the cloud server 300. The updated information may be used later as big data.

In an embodiment of the present disclosure, the server 300 may collect information on the air contamination level in a specific area or a specific building from the plurality of portable air purifiers 110 and the wearable device 112 to guide each device user. The air contamination level may actually notify the air contamination level of a specific area separately from the weather forecast, and the contaminated air exposure level inferring apparatus 100 may be used to receive the air contamination level information of the specific area from the server 300 to infer the contaminated air exposure level.

The embodiments of the present disclosure described above may be implemented through computer programs executable through various components on a computer, and such computer programs may be recorded in computer-readable media. For example, the recording media may include magnetic media such as hard disks, floppy disks, and magnetic media such as a magnetic tape, optical media such as CD-ROMs and DVDs, magneto-optical media such as floptical disks, and hardware devices specifically configured to store and execute program commands, such as ROM, RAM, and flash memory.

Meanwhile, the computer programs may be those specially designed and constructed for the purposes of the present disclosure or they may be of the kind well known and available to those skilled in the computer software arts. Examples of program code include both machine codes, such as produced by a compiler, and higher level code that may be executed by the computer using an interpreter.

As used in the present application (especially in the appended claims), the terms "a/an" and "the" include both singular and plural references, unless the context clearly conditions otherwise. Also, it should be understood that any numerical range recited herein is intended to include all sub-ranges subsumed therein (unless expressly indicated otherwise) and accordingly, the disclosed numeral ranges include every individual value between the minimum and maximum values of the numeral ranges.

Operations constituting the method of the present disclosure may be performed in appropriate order unless explicitly described in terms of order or described to the contrary. The present disclosure is not necessarily limited to the order of operations given in the description. All examples described herein or the terms indicative thereof ("for example," etc.) used herein are merely to describe the present disclosure in greater detail. Accordingly, it should be understood that the scope of the present disclosure is not limited to the example embodiments described above or by the use of such terms unless limited by the appended claims. Accordingly, it should be understood that the scope of the present disclosure is not limited to the example embodiments described above or by the use of such terms unless limited by the appended claims. Also, it should be apparent to those skilled in the art that various alterations, substitutions, and modifications may be made within the scope of the appended claims or equivalents thereof.

Accordingly, technical ideas of the present disclosure are not limited to the above-mentioned embodiments, and it is intended that not only the appended claims, but also all changes equivalent to claims, should be considered to fall within the scope of the present disclosure.

What is claimed is:

1. A method comprising:
   receiving a dust concentration measured by a dust sensor of a wearable device or a portable air purifier;
   inputting data on the dust concentration to an analysis model to thereby determine whether an air contamination level of an area, in which the portable air purifier or a user carrying the wearable device is located, exceeds a predetermined threshold by comparing the dust concentration per time to a predetermined value;
   based on the air contamination level exceeding the predetermined threshold, notifying the user of information on the air contamination level, or transferring the information on the air contamination level to an external home appliance; and
   instructing the external home appliance to automatically operate according to the air contamination level,
   wherein the analysis model comprises a learned artificial intelligence model that is trained to determine the air contamination level,
   wherein the learned artificial intelligence model comprises an exposure level classifying engine that is trained with learning data comprising dust concentration data on a plurality of dust concentrations and label data obtained by matching the dust concentration data to labels of the air contamination level,
   wherein the method further comprises outputting the air contamination level from the learned artificial intelligence model,
   wherein receiving the dust concentration comprises receiving, from the portable air purifier, information on an operation intensity of a fan of the portable air purifier, and
   wherein the air contamination level is determined based on the dust concentration per time and the operation intensity of the fan of the portable air purifier.

2. The method of claim 1, wherein receiving the dust concentration comprises receiving, from the portable air purifier, a usage amount of a filter of the portable air purifier, and
   wherein the air contamination level is determined based on the dust concentration received from the dust sensor of the portable air purifier and the usage amount of the filter.

3. The method of claim 2, further comprising:
   applying the data on the dust concentration and the usage amount of the filter to the learned artificial intelligence model that is trained to determine the air contamination level; and
   outputting the air contamination level from the learned artificial intelligence model.

4. The method of claim 3, wherein the learning data further comprise usage amounts of the filter used based on operation of the portable air purifier, and
   wherein the label data are obtained by matching the usage amounts of the filter to labels of the air contamination level.

5. The method of claim 4, wherein the exposure level classifying engine is machine-learned by Classification or Regression analysis.

6. A non-transitory computer readable recording medium having stored thereon a computer program which, when executed by at least one processor, causes performance of computer-executable instructions comprising:
   receiving a dust concentration measured by a dust sensor of a wearable device or a portable air purifier;
   inputting data on the dust concentration to an analysis model to thereby determine whether an air contamination level of an area, in which the portable air purifier or a user carrying the wearable device is located, exceeds a predetermined threshold based by comparing the dust concentration per time to a predetermined value;
   based on the air contamination level exceeding the predetermined threshold, notifying the user of information on the air contamination level or transferring the information on the air contamination level to an external home appliance; and
   instructing the external home appliance to automatically operate according to the air contamination level,
   wherein the analysis model comprises a learned artificial intelligence model that is trained to determine the air contamination level,
   wherein the learned artificial intelligence model comprises an exposure level classifying engine that is trained with learning data comprising dust concentration data on a plurality of dust concentrations and label data obtained by matching the dust concentration data to labels of the air contamination level, and
   wherein the instructions further comprise outputting the air contamination level from the learned artificial intelligence model.

7. An apparatus comprising:
   at least one processor configured to:
      receive a dust concentration measured from a dust sensor of a wearable device or a portable air purifier;
      input data on the dust concentration to an analysis model to thereby determine whether an air contamination level of an area, in which the portable air purifier or a user carrying the wearable device is located, exceeds a predetermined threshold by comparing the dust concentration per time to a predetermined value;

transfer information on the air contamination level to an external home appliance based on the air contamination level exceeding the predetermined threshold; and instruct the external home appliance to automatically operate according to the air contamination level, wherein the at least one processor is further configured to:

receive, from the portable air purifier, information on an operation intensity of a fan of the portable air purifier, and determine the air contamination level based on the dust concentration per time and the operation intensity of the fan of the portable air purifier, wherein the analysis model comprises a learned artificial intelligence model that is trained to determine the air contamination level, wherein the learned artificial intelligence model comprises an exposure level classifying engine that is trained with learning data comprising dust concentration data on a plurality of dust concentrations and label data obtained by matching the dust concentration data to labels of the air contamination level, and wherein the at least one processor is further configured to output the air contamination level from the learned artificial intelligence model.

8. The apparatus of claim 7, wherein the at least one processor is configured to:

receive, from the portable air purifier, a usage amount of a filter of the portable air purifier, and determine the air contamination level based on the dust concentration received from the dust sensor of the portable air purifier and the usage amount of the filter.

9. The apparatus of claim 7, wherein the at least one processor is configured to notify the user of information on at least one of the dust sensor, an air quality improvement effect by the portable air purifier, or the air contamination level.

10. The apparatus of claim 8, wherein the at least one processor is configured to:

apply the data on the dust concentration and the usage amount of the filter to the learned artificial intelligence model that is trained to determine the air contamination level, and output the air contamination level from the learned artificial intelligence model, wherein the learning data further comprise usage amounts of the filter used based on operation of the portable air purifier, and wherein the label data are obtained by matching the usage amounts of the filter to labels of the air contamination level.

11. The apparatus of claim 10, wherein the exposure level classifying engine is learned by Classification and Regression analysis with the learning data comprising the dust concentration data and the label data.

12. A system comprising:

an apparatus configured to provide operation information of a wearable device or a portable air purifier; and a server configured to receive the operation information of the wearable device or the portable air purifier and to train an artificial intelligence model based on the operation information, wherein the apparatus comprises at least one processor that is configured to:

receive a dust concentration measured from a dust sensor of the wearable device or the portable air purifier, input data on the dust concentration to an analysis model received from the server to thereby determine whether an air contamination level of an area, in which the portable air purifier or a user carrying the wearable device is located, exceeds a predetermined threshold by comparing the dust concentration per time to a predetermined value, the analysis model comprising a learned artificial intelligence model received from the server, transfer information on the air contamination level to an external home appliance based on the air contamination level exceeding the predetermined threshold, and instruct the external home appliance to automatically operate according to the air contamination level, and communicate with the server and transmit the dust concentration to the server, wherein the server is configured to:

generate the learned artificial intelligence model by training an artificial intelligence model to determine the air contamination level with learning data comprising the dust concentration, wherein the server is configured to transmit the learned artificial intelligence model to the apparatus, wherein the at least one processor is configured to determine the air contamination level through the learned artificial intelligence model received from the server, wherein the learned artificial intelligence model comprises an exposure level classifying engine that is trained with learning data comprising dust concentration data on a plurality of dust concentrations and label data obtained by matching the dust concentration data to labels of the air contamination level, and wherein the at least one processor is further configured to output the air contamination level from the learned artificial intelligence model.

* * * * *